(12) United States Patent
Yuan et al.

(10) Patent No.: US 7,041,664 B2
(45) Date of Patent: May 9, 2006

(54) 2-AMINOQUINOLINECARBOXAMIDES: NEUROKININ RECEPTOR LIGANDS

(75) Inventors: Jun Yuan, Guilford, CT (US); George Maynard, Clinton, CT (US); Alan Hutchison, Madison, CT (US)

(73) Assignee: Neurogen Corporation, Branford, CT (US)

( * ) Notice: Subject to any disclaimer, the term of this patent is extended or adjusted under 35 U.S.C. 154(b) by 108 days.

(21) Appl. No.: 10/868,136

(22) Filed: Jun. 14, 2004

(65) Prior Publication Data
US 2004/0229907 A1 Nov. 18, 2004

Related U.S. Application Data

(63) Continuation of application No. 10/115,409, filed on Apr. 3, 2002, now Pat. No. 6,894,044.

(60) Provisional application No. 60/131,025, filed on Apr. 26, 1999.

(51) Int. Cl.
C07D 401/04 (2006.01)
A61K 31/47 (2006.01)

(52) U.S. Cl. .................. 514/228.2; 546/148; 546/149; 546/168; 546/169; 544/363; 514/233.5; 514/253.06; 514/299; 514/307; 514/313; 514/314; 206/828

(58) Field of Classification Search ............... 546/159, 546/148, 149, 168, 169; 514/313, 228.2, 514/233.5, 299, 253.06, 307, 314; 544/62, 544/128, 363; 206/828
See application file for complete search history.

(56) References Cited

U.S. PATENT DOCUMENTS

| 5,340,822 | A | 8/1994 | Emonds-Alt et al. |
| 5,434,158 | A | 7/1995 | Shah |
| 6,369,053 | B1 | 4/2002 | Yuan et al. |

FOREIGN PATENT DOCUMENTS

| EP | 0 512 901 A1 | 4/1994 |
| JP | 53-44577 | 4/1992 |
| WO | WO 95/32948 | 12/1995 |
| WO | WO 96/02509 | 2/1996 |
| WO | WO 97/19926 | 6/1997 |
| WO | WO 97/19928 | 6/1997 |
| WO | WO 97/21680 | 6/1997 |
| WO | WO 98/41506 | 9/1998 |
| WO | WO 98/52942 | 11/1998 |

OTHER PUBLICATIONS

Batt et al., Bioorg. Med. Chem. Lett., 1998, 8, pp. 1745-1750.
Boden, Phil et al., "Use of a Dipeptide Chemical Library in the Development of Non-Peptide Tachykinin $NK_3$ Receptor Selective Antagonists", *J. Med. Chem.* 1996, 39, 1664-1675.
Buchwald et al. J. Org. Chem., 2000, 65, pp. 11444-11474.
Giardina et al., (1997) "Discovery of a Novel Class of Selective Non-Peptide Antagonists for the Human Neurokinin-3-Receptor. 1. Identification of the 4-Quinolinecarboxamide Framework", *Journal of Medicinal Chemistry*, vol. 40, pp. 1794-1807.
Jacobs et al., Org. Synth. Coll., 1955, 3, pp. 456-458.
Lyle et al., J. Org. Chem. , 1972, 37, pp. 3967-3968.

*Primary Examiner*—Zinna Northington Davis
(74) *Attorney, Agent, or Firm*—McDonnell Boehnen Hulbert & Berghoff LLP

(57) ABSTRACT

Disclosed are compounds of the formula:

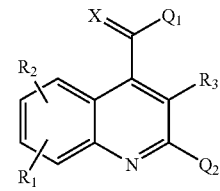

or pharmaceutically acceptable salts or pharmaceutically acceptable solvates thereof,
wherein $R_1$, $R_2$, $R_3$, X, $Q_1$ and $Q_2$ are defined herein,
which compounds are ligands for neurokinin receptors, in particular NK-3 receptors, and are therefor useful in the treatment of a wide range of diseases or disorders including, but not limited to depression, anxiety, psychosis, obesity, pain, Parkinson's disease, Alzheimer's disease, neurodegenerative diseases, movement disorders, respiratory diseases, inflammatory diseases, neuropathy, immune disorders, migraine, biliary disfunction, and dermatitis.

11 Claims, No Drawings

2-AMINOQUINOLINECARBOXAMIDES: NEUROKININ RECEPTOR LIGANDS

This is a continuation of prior application Ser. No. 10/115,409, filed Apr. 3, 2002 now U.S. Pat. No. 6,894,044.

This application claims priority from provisional application No. 60/131,025 filed Apr. 26, 1999 which is incorporated herein by reference in its entirety.

BACKGROUND OF THE INVENTION

1. Field of the Invention

This invention relates to 2-aminoquinolinecarboxamides, pharmaceutical compositions comprising them, and the use of such compounds in the treatment of certain central nervous system and peripheral diseases. The compounds of this invention are also useful as probes for the localization of cell surface receptors.

2. Description of the Related Art

The tachykinins represent a family of structurally related peptides originally isolated based upon their smooth muscle contractile and sialogogic activity. These mammalian peptides include substance P (SP), neurokinin A (NKA) and neurokinin β (NKB). Tachykinins are synthesized in the central nervous system (CNS), as well as in peripheral tissues, where they exert a variety of biological activities. Substance P can be produced from three different mRNAs (α-, β- and γ-preprotachykinin mRNAs) that arise from a single gene as a result of alternative RNA splicing, whereas NKA can be generated from either the β- or the γ-preprotachykinin mRNA through posttranslationally processed precursor polypeptides. These precursors can also be differentially processed so that amino terminally extended forms of NKA (known as neuropeptide K and neuropeptide γ) are produced. NKB is produced from a separate mRNA arising from a second gene known as preprotachykinin B.

Three receptors for the tachykinin peptides have been molecular characterized and are referred to as neurokinin-1 (NK-1), neurokinin-2 (NK-2) and neurokinin-3 (NK-3) receptors. The NK-1 receptor has a natural agonist potency profile of SP>NKA>NKB. The NK-2 receptor agonist potency profile is NKA>NKB>SP, and the NK-3 receptor agonist potency profile is NKB>NKA>SP. These receptors mediate the variety of tachykinin-stimulated biological effects that generally include 1) modulation of smooth muscle contractile activity, 2) transmission of (generally) excitatory neuronal signals in the CNS and periphery (e.g. pain signals), 3) modulation of immune and inflammatory responses, 4) induction of hypotensive effects via dilation of the peripheral vasculature, and 5) stimulation of endocrine and exocrine gland secretions. These receptors transduce intracellular signals via the activation of pertussis toxin-insensitive ($G_{aq/11}$) G proteins, resulting in the generation of the intracellular second messengers inositol 1,4,5-trisphosyphate and diacylglycerol. NK-1 receptors are expressed in a wide variety of peripheral tissues and in the CNS. NK-2 receptors are expressed primarily in the periphery, while NK-3 receptors are primarily (but not exclusively) expressed in the CNS. Recent work confirms the presence of NK-3 receptor binding sites in the human brain.

Studies measuring the localization of NKB and NK-3 receptor mRNAs and proteins, along with studies performed using peptide agonists and non-peptide NK-3 receptor antagonists, provide a rationale for using NK-3 receptor antagonists in treating a variety of disorders in both the CNS and the periphery. In the CNS, activation of NK-3 receptors has been shown to modulate dopamine and serotonin release, indicating therapeutic utility in the treatment of a variety of disorders including anxiety, depression, schizophrenia and obesity. Further, studies in primate brain detect the presence of NK-3 mRNA in a variety of regions relevant to these disorders. With regard to obesity, it has also been shown that NK-3 receptors are located on MCH-containing neurons in the rat lateral hypothalamus and zona incerta. In the periphery, administration of NKB into the airways is known to induce mucus secretion and bronchoconstriction, indicating therapeutic utility for NK-3 receptor antagonists in the treatment of patients suffering from airway diseases such as asthma and chronic obstructive pulmonary disease (COPD). Localization of NK-3 receptors in the gastrointestinal (GI) tract and the bladder indicates therapeutic utility for NK-3 receptor antagonists in the treatment of GI and bladder disorders including inflammatory bowel disease and urinary incontinence.

Both peptide and nonpeptide antagonists have been developed for each of the tachykinin receptors. The first generation of peptide antagonists for the tachykinin receptors had problems with low potency, partial agonism, poor metabolic stability and toxicity, whereas the current generation of non-peptide antagonists display more drug-like properties. Unfortunately, previous non-peptide NK-3 receptor antagonists suffer from a number of problems such as species selectivity (which limits the potential to evaluate these compounds in many appropriate disease models). New non-peptide NK-3 receptor antagonists are therefore being sought, both as therapeutic agents and as tools to further investigate the anatomical and ultrastructural distribution of NK-3 receptors, as well as the physiologic and pathophysiologic consequences of NK-3 receptor activation.

SUMMARY OF THE INVENTION

This invention relates to 2-aminoquinolinecarboxamides represented by structure Formula I:

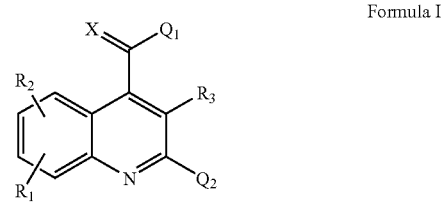

Formula I or pharmaceutically acceptable salts or pharmaceutically acceptable solvates thereof, wherein in $R_1$, $R_2$, $R_3$, X, $Q_1$ and $Q_2$ are hereinafter defined.

The invention also relates to pharmaceutical compositions comprising such compounds and the use of such compounds and compositions in the treatment of certain central nervous system and peripheral diseases or disorders.

The compounds of this invention are ligands for neurokinin receptors, in particular NK-3 receptors, and are useful in the treatment of a wide range of diseases or disorders including, but not limited to depression, anxiety, psychosis, obesity, pain, Parkinson's disease, Alzheimer's disease, neurodegenerative diseases, movement disorders, respiratory diseases, inflammatory diseases, neuropathy, immune disorders, migraine, biliary disfunction, and dermatitis.

The invention provides novel 2-aminoquinolinecarboxamides that bind selectively to neurokinin receptors, in particular NK-3 receptors. These compounds are therefore of use in the treatment of a broad array of diseases which are characterized by modulation of the neurokinin receptors, in particular NK-3 receptors.

In a separate aspect, the invention provides methods of using compounds of this invention as positive controls in assays for receptor activity and using appropriately labeled compounds of the invention as probes for the localization of receptors, particularly neurokinin-3 receptors, in tissue sections.

DETAILED DESCRIPTION OF THE INVENTION

This invention relates to 2-aminoquinolinecarboxamides, pharmaceutical compositions comprising them, and the use of such compounds in the treatment of certain central nervous system and peripheral diseases or disorders.

Accordingly, a broad embodiment of the invention is directed to compounds of Formula I:

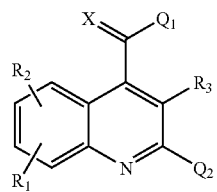

I or pharmaceutically acceptable salts or pharmaceutically acceptable solvates thereof, wherein:

$R_1$ is:

hydrogen, halogen, hydroxy, $C_{1-6}$ alkyl, —O($C_{1-6}$ alkyl), —NO$_2$, —CN, —SO$_2$NH$_2$, —SO$_2$NH($C_{1-6}$ alkyl), —SO$_2$N($C_{1-6}$ alkyl) ($C_{1-6}$ alkyl), amino, —NH ($C_{1-6}$ alkyl), —N($C_{1-6}$ alkyl)($C_{1-6}$ alkyl), —N($C_{1-6}$ alkyl)CO ($C_{1-6}$ alkyl), —NHCO$_2$($C_{1-6}$ alkyl), —N($C_{1-6}$ alkyl) CO$_2$($C_{1-6}$ alkyl), —NHSO$_2$($C_{1-6}$ alkyl), —N($C_{1-6}$ alkyl)SO$_2$($C_{1-6}$ alkyl), —SO$_2$NHCO($C_{1-6}$ alkyl), —CONHSO$_2$($C_{1-6}$ alkyl), —CON($C_{1-6}$ alkyl)($C_{1-6}$ alkyl), —CO$_2$($C_{1-6}$ alkyl), —S($C_{1-6}$ alkyl), —SO($C_{1-6}$ alkyl), or —SO$_2$($C_{1-6}$ alkyl), where each $C_{1-6}$ alkyl is a straight, branched or cyclic alkyl group optionally containing one or two double or triple bonds and optionally substituted with one or more of hydroxy, oxo, halogen, amino, or $C_{1-3}$ alkoxy;

$R_2$ and $R_3$ are independently selected from the groups consisting of:

hydrogen, halogen, hydroxy, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl) ($C_{1-8}$ alkyl), amino, —NH($C_{1-8}$ alkyl), —N($C_{1-8}$ alkyl)($C_{1-8}$ alkyl), —N($C_{1-8}$ alkyl)CO ($C_{1-8}$ alkyl), —NHCO$_2$($C_{1-6}$ alkyl), —N($C_{1-8}$ alkyl) CO$_2$($C_{1-8}$ alkyl), —NHSO$_2$($C_{1-8}$ alkyl), —N($C_{1-6}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl), —SO$_2$($C_{1-8}$ alkyl), and Ar, wherein Ar is phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, or benzopyrazolyl, each of which is optionally substituted with one or more of:

halogen, hydroxy, $C_{1-6}$ alkyl, —O($C_{1-6}$ alkyl), —NO$_2$, —CN, —SO$_2$NH$_2$, —SO$_2$NH($C_{1-6}$ alkyl), —SO$_2$N ($C_{1-6}$ alkyl)($C_{1-6}$ alkyl) amino, —NH($C_{1-6}$ alkyl), —N($C_{1-6}$ alkyl)($C_{1-6}$ alkyl), —N($C_{1-6}$ alkyl)CO($C_{1-6}$ alkyl), —NHCO$_2$($C_{1-6}$ alkyl), —N($C_{1-6}$ alkyl)CO$_2$ ($C_{1-6}$ alkyl), —NHSO$_2$($C_{1-6}$ alkyl), —N($C_{1-6}$ alkyl) SO$_2$($C_{1-6}$ alkyl), —SO$_2$NHCO($C_{1-6}$ alkyl), —CONHSO$_2$($C_{1-6}$ alkyl), —CON($C_{1-6}$ alkyl)($C_{1-6}$ alkyl), —CO$_2$($C_{1-6}$ alkyl), —S($C_{1-6}$ alkyl), —SO ($C_{1-6}$ alkyl), or —SO$_2$($C_{1-6}$ alkyl), where each $C_{1-6}$ alkyl is as defined above for $R_1$; and each $C_{1-8}$ alkyl is a straight, branched or cyclic alkyl group optionally containing one or two double or triple bonds and optionally substituted with one or more of:

(i) hydroxy, (ii) oxo, (iii) halogen, (iv) Ar, wherein Ar is as defined above, (v) —NR$_4$R$_5$, wherein R$_4$ and R$_5$ are independently selected from:

(A) hydrogen;

(B) $C_{1-6}$ alkyl, wherein $C_{1-6}$ alkyl is as defined above for $R_1$;

(C) Ar, where in Ar is as defined above;

(D) $C_{1-6}$ alkyl-Ar, wherein Ar is as defined above and Ar is attached to any position of the $C_{1-6}$ alkyl group at any position of Ar;

or R$_4$ and R$_5$ together form a 4- to 8-membered monocyclic or bicyclic nitrogen-containing ring which may contain:

(a) one or two double bonds;

(b) one or two oxo;

(c) one or two of O, S or N—R$_6$ wherein R$_6$ is hydrogen, $C_{1-6}$ alkyl, $C_{1-6}$ alkyl-Ar, wherein $C_{1-6}$ alkyl and Ar are defined as above and Ar is attached to to any position of the $C_{1-6}$ alkyl group at any position of Ar; or (d) one or two of $R_1$ where $R_1$ is as defined above;

(vi) —OR$_4$, wherein R$_4$ is as defined above;

(vii) —CONR$_4$R$_5$, wherein R$_4$ and R$_5$ are as defined above;

(viii) —SO$_2$NR$_4$R$_5$, wherein R$_4$ and R$_5$ are as defined above;

(x) —NR$_4$COR$_5$, wherein R$_4$ and R$_5$ are as defined above;

X is O, S or N—CN;

Q$_1$ and Q$_2$ are independently selected from formulas II and III:

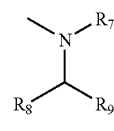

II

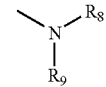

III wherein
R$_7$ is hydrogen or C$_{1-8}$ alkyl;
C$_{1-8}$ alkyl is as defined above;
R$_8$ and R$_9$ are independently selected from:
  (i) hydrogen;
  (ii) Ar', wherein Ar' is phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, or benzopyrazolyl, each of which is unsubstituted or substituted with one or more of:
    halogen, hydroxy, C$_{1-8}$ alkyl, —O(C$_{1-8}$ alkyl), —NO$_2$, —CN, —SO$_2$NH$_2$, —SO$_2$NH (C$_{1-8}$ alkyl), —SO$_2$N(C$_{1-8}$ alkyl)(C$_{1-8}$ alkyl), amino, —NH(C$_{1-8}$ alkyl), —N(C$_{1-8}$ alkyl)(C$_{1-8}$ alkyl), —N(C$_{1-8}$ alkyl)CO(C$_{1-8}$ alkyl), —NHCO$_2$(C$_{1-6}$ alkyl), —N(C$_{1-8}$ alkyl)CO$_2$(C$_{1-8}$ alkyl), —NHSO$_2$(C$_{1-8}$ alkyl), —N(C$_{1-6}$ alkyl)SO$_2$(C$_{1-8}$ alkyl), —SO$_2$NHCO(C$_{1-8}$ alkyl), —CONHSO$_2$(C$_{1-8}$ alkyl), —CON(C$_{1-8}$ alkyl)(C$_{1-8}$ alkyl), —CO$_2$(C$_{1-8}$ alkyl), —S(C$_{1-8}$ alkyl) —SO(C$_{1-8}$ alkyl), or —SO$_2$(C$_{1-8}$ alkyl), wherein C$_{1-8}$ alkyl and C$_{1-6}$ alkyl are as defined above;
  (iii) C$_{1-8}$ alkyl, wherein said C$_{1-8}$ alkyl is as defined above,
  (iv) —COR$_4$, wherein R$_4$ is as defined above,
  (v) —CONR$_4$R$_5$, wherein R$_4$ and R$_5$ are as defined above,
  (vi) —SO$_2$NR$_4$R$_5$, wherein R$_4$ and R$_5$ are as defined above.
or R$_8$ and R$_9$ together form a 4- to 8-membered monocyclic or bicyclic ring which may contain:
  (a) one or two double bonds;
  (b) one or two oxo;
  (c) one or two O, S or N—R$_{10}$ wherein R$_{10}$ is hydrogen, C$_{1-8}$ alkyl, C$_{1-8}$ alkyl-Ar', wherein C$_{1-8}$ alkyl and Ar' are defined as above and Ar' may be attached to C$_{1-8}$ alkyl at any position; or
  (d) one or two R$_1$ groups.

Preferred compounds of the invention include those of Formula I where Q$_1$ is a group of the formula I-g:

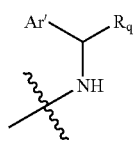

I-g where
Ar' is phenyl optionally substituted with one or more of halogen, hydroxy, C$_{1-8}$ alkyl, —O(C$_{1-8}$ alkyl), —NO$_2$, —CN, amino, —NH(C$_{1-8}$ alkyl), —N(C$_{1-8}$ alkyl)(C$_{1-8}$ alkyl), —N(C$_{1-8}$ alkyl)CO(C$_{1-8}$ alkyl), —NHCO$_2$(C$_{1-6}$ alkyl), —N(C$_{1-8}$ alkyl)CO$_2$(C$_{1-8}$ alkyl), —CON(C$_{1-8}$ alkyl)(C$_{1-8}$ alkyl), —CO$_2$(C$_{1-8}$ alkyl), wherein C$_{1-8}$ alkyl and C$_{1-6}$ alkyl are as defined above; and
R$_q$ is straight or branched chain alkyl having from 1–6 carbon atoms.

More preferred compounds of Formula I where Q$_1$ is a group of formula I-g include those where X is oxygen. Particularly preferred are such compounds where R$_1$ and R$_2$ are both hydrogen.

Formula I-g encompasses the following groups:

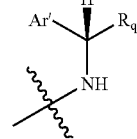

I-h

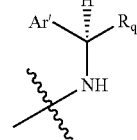

I-k where Ar' and R$_q$ carry the same definitions as given above for formula I-g.

The invention encompasses compounds having Q$_1$ groups represented by either of formulas I-h or I-k.

Other preferred compounds of Formula I include those of Formula I-A:

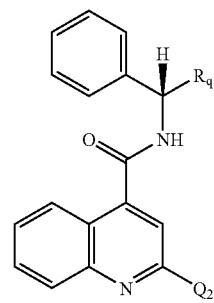

I-A where R$_q$ is straight or branched chain alkyl having from 1–6 carbon atoms; and
Q$_2$ is as defined above for Formula I.

Particularly preferred compounds of Formula I-A are those where R$_q$ is ethyl; Q$_2$ represents formula I or formula II where R$_7$ is defined as above and R$_8$ and R$_9$ are independently selected from:
  hydrogen;
  C$_{1-8}$ alkyl, wherein said C$_{1-8}$ alkyl is as defined above; or
  R$_8$ and R$_9$ together form a 4- to 8-membered monocyclic or bicyclic ring which may contain:
    (a) one or two double bonds;
    (b) one or two oxo;
    (c) one or two O, S or N—R$_{10}$ wherein R$_{10}$ is hydrogen, C$_{1-8}$ alkyl, C$_{1-8}$ alkyl-Ar', wherein C$_{1-8}$ alkyl and Ar' are defined as above and Ar' may be attached to C$_{1-8}$ alkyl at any position; or
    (d) one or two R$_1$ groups.

Still other preferred compounds of Formula I include those of Formula I-B:

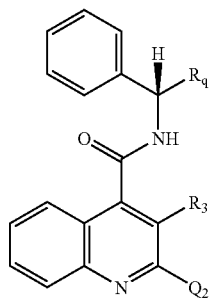

Wherein:

R_q is straight or branched chain alkyl having from 1-6 carbon atoms;

$R_3$ is $C_{1-6}$ alkyl or $C_{1-6}$ alkoxy; and $Q_2$ is as defined above for Formula I.

Particularly preferred compounds of Formula I-B are those where $R_q$ is ethyl; and $Q_2$ is a group of the formula:

wherein $R_8$ and $R_9$ together form a 4- to 8-membered monocyclic or bicyclic ring which may contain:

(a) one or two double bonds;

(b) one or two oxo;

(c) one or two O, S or N—$R_{10}$ wherein $R_{10}$ is hydrogen, $C_{1-8}$ alkyl.

The compounds of Formula I may contain one or more asymmetric centers, so that the compounds can exist in different stereoisomeric forms. All stereoisomeric forms (e.g., optical isomers) and mixtures thereof are encompassed by the invention. The compounds containing asymmetric centers can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

In addition compounds of Formula I with carbon-carbon double bonds may occur in the Z- and/or E-forms. All such isomeric forms of such compounds are encompassed within the invention. Further, such compounds may be prepared in either pure E or pure Z forms using methods known to those skilled in the art.

When any variable (e.g. $C_{1-6}$ alkyl, $C_{1-8}$ alkyl, $R_1$–$R_9$, $Q_1$ or $Q_2$) occurs more than one time in Formula I, its definition on each occurrence is independent of its definition at every other occurrence.

As used herein, the term "alkyl" includes those alkyl groups of a designed number of carbon atoms. Examples of "alkyd" include methyl, ethyl, propyl, isopropyl, butyl, iso-, sec- and tert-butyl, pentyl, hexyl, heptyl, 3-ethylbutyl, cyclopropyl, cyclobutyl, cyclopentyl, cyclohexyl, cycloheptyl, norbornyl, and the like. When reference is made herein to $C_{1-6}$ alkyl or $C_{1-8}$ alkyl which it may contain one or two double or triple bond it is understood that at least two carbons are present in the alkyl for one double or triple bond, and at least four carbons for two double or triple bonds. "Alkoxy" represents an alkyl group of indicated number of carbon atoms attached through an oxygen bridge, such as methoxy, ethoxy, propoxy and isopropoxy.

By "halogens" herein is meant fluorine, chlorine, bromine, and iodine. Preferred halogens are fluorine and chlorine. Particularly preferred is fluorine.

As used herein, the terms "patient" and "patients" refer to humans as well as other mammals including pets such as dogs and cats and livestock such as cattle and sheep.

By $C_{1-6}$ alkyl-Ar as used herein is meant an aryl (Ar) group substituted on an alkyl group which is in turn connected to the parent structure. Examples of such groups are benzyl, phenethyl, 1-naphthylmethyl, 2-pyridylmethyl, and 3-pyimidin-2-ylpropyl.

This invention also includes methods for using compounds of Formula I to treat diseases or disorders in patients in which mediation by NK-3 receptors is of importance.

The compounds of this invention are ligands for neurokinin receptors, in particular NK-3 receptors, and are useful in the treatment of a wide range of diseases or disorders of the central nervous system (CNS) and periphery in mammals in which modulation of NK-3 receptors is of importance. These include depression, anxiety, panic disorder, obsessive compulsive disorder, psychosis and schizophrenia, neurodegenerative disorders such as dementia, Alzheimer's diseases, Parkinson's disease, Huntington's disease, stress related somatic disorders, reflex sympathetic dystrophy, dysthmic disorders, obesity, eating disorders, drug and alcohol addiction, movement disorders, convulsive disorders such as epilepsy, migraine, headache, multiple sclerosis and other demyelinating diseases, AIDS related neuropathy, chemotherapy-induced neuropathy and neuralgia, diabetic or peripheral neuropathy, neurogenic inflammation, inflammatory pain, neuropathic pain, and other types of chronic or acute pain, Reynaud's disease, vasodilation, vasospasm, angina, asthma, chronic obstructive pulmonary diseases, airway hyperreactivity, cough, allergic rhinitis, bronchospasm, bronchopneumonia, ocular inflammation, inflammatory bowel disease, Crohn's disease, ulcerative colitis, biliary disfunction, skin disorders and itch, hypersensitivity disorders, atopic dermatitis, contact dermatitis, cutaneous wheal and flare, renal disorders, urinary incontinence, immune system disorders and adverse immunological reactions, fibrositis, osteoarthritis, eosinophilic fascioliasis, and scleroderma.

The present invention also pertains to methods of inhibiting the binding of neurokinin to the NK-3 receptor which methods involve contacting a compound of the invention with cells expressing NK-3 receptors, wherein the compound is present at a concentration sufficient to inhibit neurokinin binding to cells expressing a cloned human NK-3 receptor in vitro. This method includes inhibiting the binding of neurokinin to NK-3 receptors in vivo, e.g., in a patient given an amount of a compound of Formula I that would be sufficient to inhibit the binding of neurokinin to NK-3 receptors in vitro. The amount of a compound that would be sufficient to inhibit the binding to neurokinin to the NK-3 receptor may be readily determined via an NK-3 receptor binding assay, such as the assay described in Example 35.

The present invention also pertains to methods for altering the signal-transducing activity of NK-3 receptors, said method comprising exposing cells expressing such receptors to an effective amount of a compound of the invention. This method includes altering the signal-transducing activity of NK-3 receptors in vivo, e.g., in a patient given an amount of a compound of Formula I that would be sufficient to alter the signal-transducing activity of NK-3 receptors in vitro. The amount of a compound that would be sufficient to alter the signal-transducing activity of NK-3 receptors may be determined via an NK-3 receptor signal transduction assay, such as the assay described in Example 36.

The NK-3 antagonist compounds provided by this invention and labeled derivatives thereof are also useful as standards and reagents in determining the ability of a potential pharmaceutical to bind to the NK-3 receptor.

Labeled derivatives the NK-3 antagonist compounds provided by this invention are also useful as radiotracers for positron emission tomography (PET) imaging or for single photon emission computerized tomography (SPECT).

If the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be employed to prepare non-toxic pharmaceutically acceptable addition salts of the compounds encompassed by Formula I.

Non-toxic pharmaceutical salts include salts of acids such as hydrochloric, phosphoric, diphosphoric, hydrobromic, stearic, sulfuric, sulfinic, formic, fumaric, toluenesulfonic, methanesulfonic, nitric, salicylic, 2-hydroxyethylsulfonic, benzoic, citric, tartaric, lactic, malic, maleic, hydroiodic, alkanoic such as acetic, HOOC—$(CH_2)_n$—ACOOH where n is 0–4, and the like. Those skilled in the art will recognize a wide variety of non-toxic pharmaceutically acceptable addition salts. Similarly, pharmaceutically acceptable cations include, but are not limited to sodium, potassium, calcium, aluminum, lithium and ammonium.

The present invention also encompasses the prodrugs of the compounds of Formula I. Those skilled in the art will recognize various synthetic methodologies that may be employed to prepare non-toxic pharmaceutically acceptable prodrugs of the compounds encompassed by Formula I. See for example N. Bodor, Drugs of the Future, 1981, 6, 165–182, and H. Bundgaard, Advanced Drug Delivery Reviews, 1989, 3, 39–65.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preserva tives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such, materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of schizophrenia, depression, or obesity a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention have certain pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat periphereal disorders are generally preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

The present invention also pertains to packaged pharmaceutical compositions for treating disorders responsive to NK-3 receptor modulation, e.g., treatment of schizoprenia, depression, or chronic pulmonary obstructive disorder by NK-3 receptor modulation. The packaged pharmaceutical compositions include a container holding a therapeutically effective amount of at least one NK-3 receptor modulator as described supra and instructions (e.g., labeling) indicating the contained NK-3 receptor ligand is to be used for treating a disorder responsive to NK-3 receptor modulation in the patient.

Compounds of Formula I wherein X is O are prepared by the method described in Scheme I.

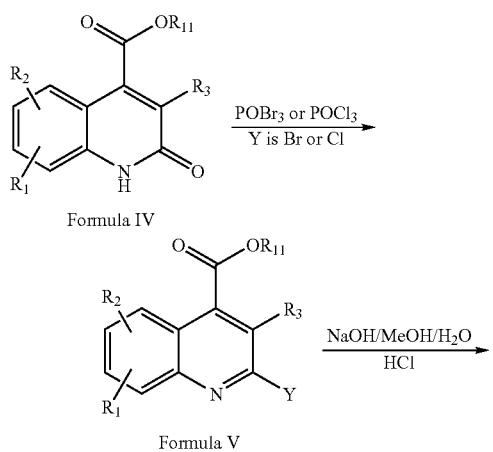

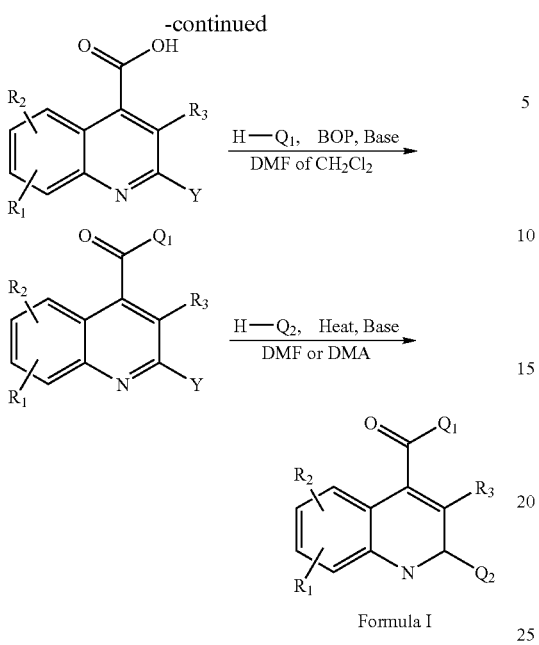

In Scheme I, $R_1$, $R_2$, $R_3$, $Q_1$ and $Q_2$ are as defined above for Formula I, and $R_{11}$ is methyl, ethyl or benzyl. BOP is benzotriazol-1-yloxytris(dimethylamino)-phosphonium-hexafluoro-phosphate. Base is triethylamine, diisoproyl-ethylamine, N-methylmorpholine or other suitable organic base. DMF is dimethylformide. DMA is dimethylacetamide. Heat as used herein means elevated temperature, such as, for example, 40 to 250° C.

Compounds of the invention where X is S or N—CN can be prepared using similar reactions. Alternatively, the compounds of Formula I where X is O can be converted to the corresponding compounds were X is S or N—CN.

Compounds of Formula IV are prepared using literature procedures several publications including Jacobs, T. L. et al.; Org. Synth. Coll. 1955, Vol. 3, 456–58 and Lyle R. E. et al. J. Org. Chem. 1972, 37, 3967–68 if they are not commercially available. Compounds of Formula V are prepared by a method described in Batt D. G. et al. Bioorg. Med. Chem. Lett. 1998, 8, 1745–50. Those skilled in the art will recognize that in certain instances it will be necessary to utilize compounds of Formula IV bearing protecting groups and that these groups can be removed in a subsequent reaction to yield compounds of Formula I as described in "Protective Groups in Organic Synthesis", 2nd Ed., Greene, T. W. and related publications.

In some situations, the replacement of Y with $Q_2$ or a protected form of $Q_2$ may be facilitated by use of a palladium catalyst as described in Buchwald, S. L. et al in J. Org. Chem. 2000, 65, 1144–57 and 1158–74. Typical conditions for this reaction include but are not limited to treatment of the 2-chloro or 2-bromoquinoline derivative with $Q_2H$, sodium tert-butoxide, catalytic tris(dibenzylideneacetone)-dipalladium(0) and catalytic BINAP ([1,1'-bisnaphthalene]-2,2'-diylbis(diphenylphosphine)) in toluene at 50–120° C. These reaction conditions are often useful for efficient conversion of Y to $Q_2$ when $R_3$ is not hydrogen.

Those having skill in the art will recognize that the starting materials, solvents, and other reaction conditions may be varied and additional steps employed to produce compounds encompassed by the present invention. In some cases protection of certain reactive functionalities may be necessary to achieve some of the above transformations. In general the need for such protecting groups will be apparent to those skilled in the art of organic synthesis as well as the conditions necessary to attach and remove such groups.

The invention is illustrated further by the following examples, which are not to be construed as limiting the invention in scope or spirit to the specific procedures described in them.

The disclosures of all articles and references mentioned in this document, including patents, are incorporated herein by reference.

EXAMPLE 1

(S)-N-(α-Ethylphenyl)-2-bromoquinoline-4-carboxamide

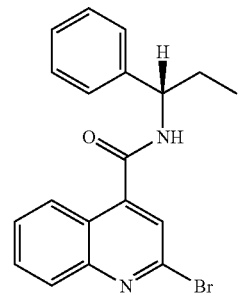

A mixture of methyl 2-bromoquinolinecarboxylate (7.2 g) and NaOH (1.1 g) in 15 mL of methanol and 15 mL of water is stirred at 50° C. until TLC indicates the disappearance of starting material. After cooling, the methanol is evaporated and the mixture is treated with 28 mL of 1N HCl, the solid is collected by filtration and dried to afford 6.1 g of 2-bromoquinoline-4-carboxylic acid.

To a solution of 2-bromoquinoline-4-carboxylic acid (2.6 g) in 25 mL of DMF containing is added BOP (5.0 g), followed by (S)-1-phenylpropylamine (2.8 g). The reaction mixture is stirred overnight at room temperature. The mixture is diluted with 20 mL of $CH_2Cl_2$, then washed with aqueous $NaHCO_3$, aqueous citric acid and brine. After drying over $Na_2SO_4$ the solvent is evaporated to afford the corresponding compound is obtained as a white solid.

EXAMPLE 2

(S)-N-(α-Ethylphenyl)-2-(pyrrolidin-1-yl)-quinoline-4-carboxamide

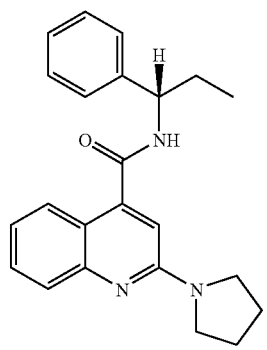

A solution of (S)-N-(α-Ethylphenyl)-2-bromoquinoline-4-carboxamide (500 mg), pyrroline (1 mL) and triethylamine (1 mL) in 5 mL of DMF in a sealed tube is heated with stirring for 8 hours. The reaction mixture is poured into ice-water. The product is collected by filtration, washed with water and dried. The corresponding compound is obtained as a tan solid.

The following examples listed in Table 1 are prepared using procedures analogous to those set forth above. MS data are given as [MH]+. LC-MS data are given as HPLC retention times and [MH]+. The HPLC retention times shown in Table 1 are obtained essentially according to the method described in Example 1.

TABLE 1

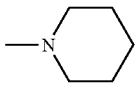

| Example | R$_3$ | —Q$_2$ | Compound Name | HPLC retention time (min) | [MH]+ |
|---|---|---|---|---|---|
| 3 | H | 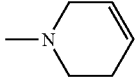 | (S)-N-(α-ethylphenyl)-2-(piperidin-1-yl)-quinoline-4-carboxamide | NA* | 374 |
| 4 | H | 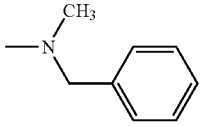 | (S)-N-(α-ethylphenyl)-2-(1,2,5,6-tetrahydropyridin-1-yl)-quinoline-4-carboxamide | 2.17 | 372 |
| 5 | H | 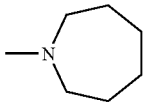 | (S)-N-(α-ethylphenyl)-2-(N,N-methylbenzylamino)-quinoline-4-carboxamide | 2.30 | 410 |
| 6 | H | 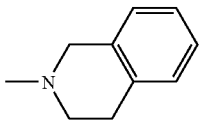 | (S)-N-(α-ethylphenyl)-2-(homopiperidin-1-yl)-quinoline-4-carboxamide | 2.23 | 388 |
| 7 | H | 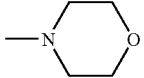 | (S)-N-(α-ethylphenyl)-2-(1,2,3,4-tetrahyroisoquinolin-2-yl)-quinoline-4-carboxamide | 2.30 | 422 |
| 8 | H | 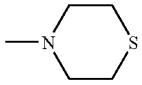 | (S)-N-(α-ethylphenyl)-2-(morpholin-4-yl)-quinoline-4-carboxamide | 2.09 | 376 |
| 9 | H | 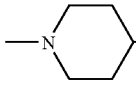 | (S)-N-(α-ethylphenyl)-2-(thiomorpholin-4-yl)-quinoline-4-carboxamide | 2.17 | 392 |
| 10 | H |  | (S)-N-(α-ethylphenyl)-2-(4-methylpiperidine-1-yl)-quinoline-4-carboxamide | 2.26 | 389 |

TABLE 1-continued

| Example | R₃ | —Q₂ | Compound Name | HPLC retention time (min) | [MH]⁺ |
|---|---|---|---|---|---|
| 11 | H | 3,3-dimethylpiperidin-1-yl | (S)-N-(α-ethylphenyl)-2-(3,3-dimethylpiperidin-1-yl)-quinoline-4-carboxamide | 2.31 | 402 |
| 12 | H | aza-1,4-dioxaspiro[4.5]decan-8-yl | (S)-N-(α-ethylphenyl)-2-(aza-1,4-dioxaspiro[4.5]decanyl-8-yl)-quinoline-4-carboxamide | 2.17 | 432 |
| 13 | H | N-methyl-N-n-butylamino | (S)-N-(α-ethylphenyl)-2-(N-methyl-N-n-butylamino)-quinoline-4-carboxamide | 2.27 | 376 |
| 14 | H | 3,5,5-trimethylhomopiperidin-1-yl | (S)-N-(α-Ethylphenyl)-2-(3,,5,5-trimethylhomopiperidn-1-yl)-quinoline-4-carboxamide | 2.47 | 430 |
| 15 | H | 2-methylpiperidin-1-yl | (S)-N-(α-Ethylphenyl)-2-(2-methylpiperidn-1-yl)-quinoline-4-carboxamide | 2.22 | 388 |
| 16 | H | 2-ethylpiperidin-1-yl | (S)-N-(α-ethylphenyl)-2-(2-ethylpiperidn-1-yl)-quinoline-4-carboxamide | 2.27 | 402 |
| 17 | H | N-methyl-N-cyclohexylamino | (S)-N-(α-ethylphenyl)-2-(N-methyl-N-cyclohexylamino)-quinoline-4-carboxamide | 2.27 | 402 |
| 18 | H | N-n-propyl-N-cyclopropylmethylamino | (S)-N-(α-ethylphenyl)-2-(N-n-propyl-N-cyclopropylmethylamino)-quinoline-4-carboxamide | 2.29 | 402 |

TABLE 1-continued

| Example | R₃ | —Q₂ | Compound Name | HPLC retention time (min) | [MH]⁺ |
|---|---|---|---|---|---|
| 19 | H | N(CH₃)(n-butyl) | (S)-N-(α-ethylphenyl)-2-(N-ethyl-N-n-butylamino)-quinoline-4-carboxamide | 2.30 | 390 |
| 20 | H | 4-methylpiperazin-1-yl | (S)-N-(α-ethylphenyl)-2-(4-methylpiperazin-1-yl)-quinoline-4-carboxamide | 2.09 | 389 |
| 21 | H | 3-hydroxypyrrolidin-1-yl | (S)-N-(α-ethylphenyl)-2-(3-hydroxypyrrolidin-1-yl)-quinoline-4-carboxamide | 2.07 | 376 |
| 22 | H | (S)-2-methoxymethyl-pyrrolidin-1-yl | (S)-N-(α-ethylphenyl)-2-[(S)-2-methoxymethyl-pyrrolidin-1-yl]-quinoline-4-carboxamide | 2.18 | 404 |
| 23 | H | (S)-2-hydroxymethylpyrrolidin-1-yl | (S)-N-(α-ethylphenyl)-2-[(S)-2-hydroxymethylpyrrolidin-1-yl]-quinoline-4-carboxamide | 2.09 | 390 |
| 24 | H | 2-carboxypyrrolidin-1-yl | (S)-N-(α-ethylphenyl)-2-(2-carboxypyrrolidin-1-yl)-quinoline-4-carboxamide | 2.12 | 404 |
| 25 | H | 3-hydroxymethylpiperidin-1-yl | (S)-N-(α-ethylphenyl)-2-(3-hydroxymethypiperidin-1-yl)-quinoline-4-carboxamide | 2.13 | 404 |
| 26 | H | 2-hydroxymethylpiperidin-1-yl | (S)-N-(α-ethylphenyl)-2-(2-hydroxymethypiperidin-1-yl)-quinoline-4-carboxamide | NA | 404 |

TABLE 1-continued

| Example | R₃ | —Q₂ | Compound Name | HPLC retention time (min) | [MH]⁺ |
|---|---|---|---|---|---|
| 27 | H | 3-hydroxypiperidin-1-yl | (S)-N-(α-ethylphenyl)-2-(3-hydroxypiperidin-1-yl)-quinoline-4-carboxamide | 2.09 | 390 |
| 28 | H | 2-(1-hydroxyethyl)piperidin-1-yl | (S)-N-(α-ethylphenyl-2-[2-(1-hydroxyethy)piperidin-1-yl]-quinoline-4-carboxamide | NA | 418 |
| 29 | H | N-α-methylbenzylamino | (S)-N-(α-Ethylphenyl)-2-(N-α-methylbenzylamino)-quinoline-4-carboxamide | NA | 410 |
| 30 | H | azabicyclo[3.2.2]nonan-3-yl | (S)-N-(α-Ethylphenyl)-2-(azabicyclo[3.2.2]nonan-3-yl)-quinoline-4-carboxamide. | 2.30 | 414 |
| 31 | CH₃ | pyrrolidin-1-yl | (S)-N-(α-Ethylphenyl)-3-methyl-2-(pyrrolidin-1-yl)-quinoline-4-carboxamide | NA | 374 |
| 32 | CH₃ | piperidin-1-yl | (S)-N-(α-Ethylphenyl)-3-methyl-2-(piperidin-1-yl)-quinoline-4-carboxamide | NA | 388 |
| 33 | OCH₃ | pyrrolidin-1-yl | (S)-N-(α-Ethylphenyl)-3-methoxy-2-(pyrrolidin-1-yl)-quinoline-4-carboxamide | NA | NA |
| 34 | OCH₃ | piperidin-1-yl | (S)-N-(α-Ethylphenyl)-3-methoxy-2-(piperidin-1-yl)-quinoline-4-carboxamide | NA | NA |

NA: not determined

The compound of Example 33 can be prepared according to the following procedure.

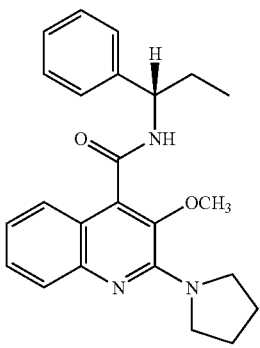

A solution of (S)-N-(α-Ethylphenyl)-2-bromo-3-methoxyquinoline-4-carboxamide (500 mg), pyrroline (106 mg), sodium tert-butoxide (1.75 mmol), $Pd_2(dba)_3$ (0.003 mmol) and BINAP (0.0094 mmol) in toluene (2.5 ml) under argon is immersed in an oil bath at 80° C. with magnetic stirring. After complete consumption of starting bromide, the reaction mixture is allowed to cool to ambient temperature, diluted with ethyl acetate (10 ml), filtered, concentrated and purified by chromatography on silica gel to yield the desired product.

The compound of Example 34 can be prepared according to the following procedure.

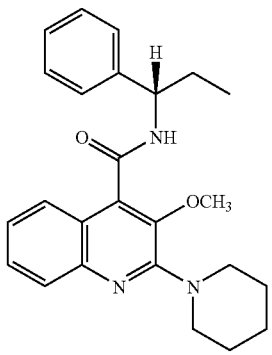

A solution of (S)-N-(α-Ethylphenyl)-2-bromo-3-methoxyquinoline-4-carboxamide (500 mg), piperidine (128 mg), sodium tert-butoxide (1.75 mmol), $Pd_2(dba)_3$ (0.003 mmol) and BINAP (0.0094 mmol) in toluene (2.5 ml) under argon is immersed in an oil bath at 80° C. with magnetic stirring. After complete consumption of starting bromide, the reaction mixture is allowed to cool to ambient temperature, diluted with ethyl acetate (10 ml), filtered, concentrated and purified by chromatography on silica gel to yield the desired product.

EXAMPLE 35

NK-3 Receptor Binding Assay

The following assay is a standard assay of NK3 receptor binding, which is used to determine the NK-3 receptor binding affinity of compounds.

Assays are performed as described in Krause et al (Proc. Natl. Acad. Sci. USA 94: 310–315, 1997). The NK-3 receptor complementary DNA was cloned from human hypothalamic RNA using standard procedures. The receptor cDNA was inserted into the expression vector $pM^2$ to transfect the mammalian Chinese hamster ovary cell line, and a stably expressing clonal cell line was isolated, characterized and used for the current experiments. Cells are grown in minimal essential medium alpha containing 10% fetal bovine serum and 0.8 mg G418 per ml. Cells were liberated from cell culture plates with No-zyme (PBS base, JRH Biosciences), and harvested by low speed centrifugation. The cell pellet was homogenized in TBS (0.05 m TrisHCl, 120 mM NaCl, pH 7.4) with a Polytron homogenizer at setting 5 for 20 seconds, and total cellular membranes were isolated by centrifugation at 47,500×g for 10 minutes. The membrane pellet was resuspended by homogenization with the Polytron as above, and the membranes were isolated by centrifugation at 47,500×g for 10 minutes. This final membrane pellet was resuspended in TBS at a protein concentration of 350 μg/ml.

Receptor binding assays contain a total volume of 200 μl containing 50 μg membrane protein, 0.15 nM $^{125}$I-methylPhe$^7$-neurokinin B, drug or blocker in TBS containing 1.0 mg/ml bovine serum albumen, 0.2 mg/ml bacitracin, 20 μg/ml leupeptin and 20 μg/ml chymostatin. Incubations are carried out for 2 hours at 4°, and the membrane proteins are harvested by passing the incubation mixture by rapid filtration over presoaked GF/B filters to separate bound from free ligand. The filters are presoaked in TBS containing 2% BSA and 0.1% Tween 20. After filtration of the incubation mixture, filters are rinsed 4 times with ice-cold TBS containing 0.01% sodium dodecyl sulfate and counted in a β-plate scintillation counter. One μM methylPhe$^7$-neurokinin B is added to some tubes to determine nonspecific binding. Data are collected in duplicate determinations, averaged, and the percent inhibition of total specific binding is calculated. The total specific binding is the total binding minus the nonspecific binding. In many cases, the concentration of unlabeled drug is varied and total displacement curves of binding are carried out. Data are converted to a form for the calculation of $IC_{50}$ and Hill coefficient (nH). Compounds of Formula I display $IC_{50}$ values less than 5 μM. Preferred compounds of Formula I display $IC_{50}$ values of less than 1 μM, more preferred compounds of Formula I display $IC_{50}$ values of less than 1 μM, still more preferred compounds of Formula I display $IC_{50}$ values of less than 100 nM, and particularly preferred compounds of Formula I display $IC_{50}$ values of less than 10 nM.

EXAMPLE 36

Assay for NK-3 Functional Activity

Calcium Mobilization Assays:

The human NK-3 bearing Chinese hamster ovary cells are grown in minimal essential media supplemented with 250 ug/ml G418, 10% fetal bovine serum and 25 mM Hepes, pH=7.4. Forty eight hours prior to the day of assay, the cells are plated in fresh media that does not contain the G418. On the day of assay, cells grown to 70–90% confluency in 96-well plates are washed with Krebs-Ringer buffer (25 mM HEPES, 5 mM KCl, 0.96 mM $NaH_2PO_4$, 1 mM $MgSO_4$, 2 mM $CaCl_2$, 5 mM glucose, 1 mM probenecid, pH 7.4) and are then incubated for 1–2 hours in the above buffer supplemented with Fluo3-AM (2.5 to 10 μg/ml; Teflabs) at 37 degrees C. in an environment containing 5% $CO_2$. The wells are then washed twice with Krebs Ringers HEPES buffer. Agonist-induced (methylPhe7-neurokinin B) calcium mobilization is monitored using a FLIPR (Molecular Devices) instrument. The agonist is added to the cells and fluorescence responses are continuously recorded for up to 5 min. For the examination of antagonist drug candidates, compounds are preincubated with the cells for up to 30 min. prior to administration of the methylPhe7-neurokinin B agonist usually at a concentration that brings about a 50% maximal activity. Responses are recorded for times up to 5 min. Kaleidagraph software (Synergy Software, Reading, Pa.) is utilized to fit the data to the equation y=a*(1/(1+(b/x)c)) to determine the $EC_{50}$ value or $IC_{50}$ value for the response. In this equation, y is the maximum fluorescence signal, x is the concentration of the agonist or antagonist, a is the $E_{max}$, b corresponds to the $EC_{50}$ or $IC_{50}$ value, and, finally, c is the Hill coefficient.

EXAMPLE 37

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). A commercial laboratory specializing in custom synthesis of radiolabeled probe compounds conveniently carries out synthesis of such radiolabeled probes. Such laboratories include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium-labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

EXAMPLE 38

Use of Compounds of the Invention as Probes for Detecting NK-3 Receptors in Cultured Cells and Tissue Samples (e.g., Tissue Sections)

Receptor autoradiography (receptor mapping) of NK-3 receptors in cultured cells or tissue samples is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A packaged pharmaceutical composition comprising a compound of the formula:

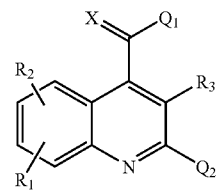

or a pharmaceutically acceptable salt or pharmaceutically acceptable solvate thereof, in a container and instructions for using the composition to treat a patient suffering from anxiety, depression, schizophrenia, obesity, chronic pulmonary obstructive disorder, or pain wherein:

$R_1$ is selected from:
hydrogen, halogen, hydroxy, $C_{1-6}$alkyl, —O($C_{1-6}$ alkyl), —$NO_2$, —CN, —$SO_2NH_2$, —$SO_2NH(C_{1-6}$alkyl), —$SO_2N(C_{1-6}$alkyl)($C_{1-6}$alkyl), amino, —NH ($C_{1-6}$alkyl), —N($C_{1-6}$alkyl)($C_{1-6}$alkyl), —N($C_{1-6}$alkyl)CO($C_{1-6}$alkyl), —$NHCO_2(C_{1-6}$ alkyl), —N($C_{1-6}$alkyl)$CO_2(C_{1-6}$alkyl), —$NHSO_2(C_{1-6}$ alkyl), —N($C_{1-6}$alkyl)$SO_2(C_{1-6}$alkyl), —$SO_2NHCO$ ($C_{1-6}$alkyl), —$CONHSO_2(C_{1-6}$alkyl), —$CON(C_{1-6}$ alkyl)($C_{1-6}$alkyl), —$CO_2(C_{1-6}$alkyl), —$S(C_{1-6}$alkyl), —$SO(C_{1-6}$alkyl), or —$SO_2(C_{1-6}$ alkyl),
wherein said $C_{1-6}$alkyl may be straight, branched or cyclic, may contain one or two double or triple bonds, unsubstituted or substituted with one or more substituents selected from: hydroxy, oxo, halogen, amino, and $C_{1-3}$ alkoxy;

$R_2$ and $R_3$ are independently selected from the group consisting of:
hydrogen, halogen, hydroxy, $C_{1-8}$alkyl, —O($C_{1-8}$ alkyl), —$NO_2$, —CN, —$SO_2NH_2$, —$SO_2NH(C_{1-8}$ alkyl), —$SO_2N(C_{1-8}$alkyl)($C_{1-8}$alkyl), amino, —NH ($C_{1-8}$alkyl), —N($C_{1-8}$alkyl)($C_{1-8}$alkyl), —N($C_{1-8}$ alkyl)CO($C_{1-8}$alkyl), —$NHCO_2(C_{1-6}$ alkyl), —N($C_{1-8}$alkyl)$CO_2(C_{1-8}$alkyl), —$NHSO_2(C_{1-8}$ alkyl), —N($C_{1-6}$alkyl)$SO_2(C_{1-8}$alkyl), —$SO_2NHCO$ ($C_{1-8}$alkyl), —$CONHSO_2(C_{1-8}$alkyl), —CON ($C_{1-8}$ alkyl)($C_{1-8}$alkyl), —$CO_2(C_{1-8}$alkyl), —$S(C_{1-8}$ alkyl), —$SO(C_{1-8}$alkyl), —$SO_2(C_{1-8}$alkyl), and Ar,
wherein Ar is phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzoisothiazolyl, triazolyl, tetrazolyl, pyrazolyl, or benzopyrazolyl, each of which is unsubstituted or substituted with one or more substituents selected from:
halogen, hydroxy, $C_{1-6}$alkyl, —O($C_{1-6}$alkyl), —$NO_2$, —CN, —$SO_2NH_2$, —$SO_2NH(C_{1-6}$alkyl), —$SO_2N$ ($C_{1-6}$alkyl)($C_{1-6}$alkyl), amino, —$NH(C_{1-6}$alkyl), —N($C_{1-6}$alkyl)($C_{1-6}$alkyl), —N($C_{1-6}$alkyl)CO($C_{1-6}$ alkyl), —$NHCO_2(C_{1-6}$alkyl), —N($C_{1-6}$alkyl)$CO_2$ ($C_{1-6}$alkyl), —$NHSO_2(C_{1-6}$alkyl), —N($C_{1-6}$alkyl)

SO$_2$(C$_{1-6}$alkyl), —SO$_2$NHCO(C$_{1-6}$alkyl), —CONHSO$_2$(C$_{1-6}$alkyl), —CON(C$_{1-6}$alkyl)(C$_{1-6}$ alkyl), —CO$_2$(C$_{1-6}$alkyl), —S(C$_{1-6}$alkyl), —SO(C$_{1-6}$ alkyl), or —SO$_2$(C$_{1-6}$alkyl), wherein C$_{1-6}$alkyl, is defined as above, wherein said C$_{1-8}$alkyl and said C$_{1-6}$alkyl may be straight, branched or cyclic, may contain one or two double or triple bonds, unsubstituted or substituted with one or more substituents selected from:
  (i) hydroxy,
  (ii) oxo,
  (iii) halogen,
  (iv) Ar, wherein Ar is as defined above,
  (v) —NR$_4$R$_5$, wherein R$_4$ and R$_5$ are independently selected from:
    (A) hydrogen,
    (B) C$_{1-6}$alkyl, wherein C$_{1-6}$alkyl is as defined above,
    (C) Ar, wherein Ar is as defined above,
    (D) C$_{1-6}$alkyl-Ar, wherein Ar is as defined above and Ar is attached to any position of the C$_{1-6}$alkyl at any position of Ar,
    and the groups R$_4$ and R$_5$ may be joined together to form a 4- to 8-membered monocyclic or bicyclic ring which may contain:
      (a) one or two double bonds,
      (b) one or two oxo,
      (c) one or two O, S or N—R$_6$ wherein R$_6$ is hydrogen, C$_{1-6}$alkyl, C$_{1-6}$alkyl-Ar, wherein C$_{1-6}$alkyl and Ar are defined as above and Ar is attached to C$_{1-6}$alkyl at any position,
      (d) one or two R$_1$,
  (vi) —OR$_4$, wherein R$_4$ is as defined above,
  (vii) —CONR$_4$R$_5$, wherein R$_4$ and R$_5$ are as defined above,
  (viii) —SO$_2$NR$_4$R$_5$, wherein R$_4$ and R$_5$ are as defined above,
  (ix) —NR$_4$COR$_5$, wherein R$_4$ and R$_5$ are as defined above;
X is O or S;
Q$_1$ is selected from Formulas A and B:

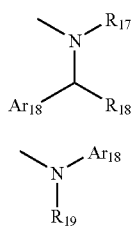

wherein
  R$_{17}$ is hydrogen or C$_{1-8}$alkyl, wherein C$_{1-8}$alkyl carries the definition assigned above,
  Ar$_{18}$ is phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, or benzopyrazolyl, each of which is unsubstituted or substituted with one or more substituents selected from:
    halogen, hydroxy, C$_{1-8}$ alkyl, —O(C$_{1-8}$alkyl), —NO$_2$, —CN, —SO$_2$NH$_2$, —SO$_2$NH(C$_{1-8}$alkyl), —SO$_2$N(C$_{1-8}$alkyl)(C$_{1-8}$alkyl), amino, —NH(C$_{1-8}$alkyl), —N(C$_{1-8}$alkyl)(C$_{1-8}$alkyl), —N(C$_{1-8}$alkyl)CO(C$_{1-8}$ alkyl), —NHCO$_2$(C$_{1-6}$alkyl), —N(C$_{1-8}$alkyl)CO$_2$(C$_{1-8}$alkyl), —NHSO$_2$(C$_{1-8}$alkyl), —N(C$_{1-8}$alkyl)SO$_2$(C$_{1-8}$alkyl), —SO$_2$NHCO(C$_{1-8}$alkyl), —CONHSO$_2$(C$_{1-8}$alkyl), —CON(C$_{1-8}$alkyl)(C$_{1-8}$ alkyl), —CO$_2$(C$_{1-8}$alkyl), —S(C$_{1-8}$alkyl), —SO(C$_{1-8}$ alkyl), —SO$_2$(C$_{1-8}$alkyl), wherein C$_{1-8}$alkyl, is defined as above,
  and R$_{18}$ are R$_{19}$ are independently
    (i) hydrogen,
    (ii) Ar$_{19}$ wherein Ar$_{19}$ carries the definition of Ar$_{18}$,
    (iii) C$_{1-8}$alkyl, wherein said C$_{1-8}$alkyl is as defined above,
    (iv) —COR$_4$, wherein R$_4$ is as defined above;
    (v) —CONR$_4$R$_5$, wherein R$_4$ and R$_5$ are as defined above,
    (vi) —SO$_2$NR$_4$R$_5$, wherein R$_4$ and R$_5$ are as defined above; and
Q$_2$ is selected from Formulas II and III:

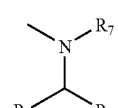

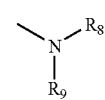

wherein R$_7$ is hydrogen or C$_{1-8}$ alkyl, wherein C$_{1-8}$ alkyl as defined above,
wherein R$_8$ and R$_9$ are independently selected from:
  (i) hydrogen,
  (ii) Ar', wherein Ar' is phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, or benzopyrazolyl, each of which is unsubstituted or substituted with one or more substituents selected from:
    halogen, hydroxy, C$_{1-8}$ alkyl, —O(C$_{1-8}$ alkyl), —NO$_2$, —CN, —SO$_2$NH$_2$, —SO$_2$NH(C$_{1-8}$ alkyl), —SO$_2$N(C$_{1-8}$ alkyl)(C$_{1-8}$ alkyl), amino, —NH(C$_{1-8}$ alkyl), —N(C$_{1-8}$ alkyl)(C$_{1-8}$ alkyl), —N(C$_{1-8}$ alkyl)CO(C$_{1-8}$ alkyl), —NHCO$_2$(C$_{1-6}$ alkyl), —N(C$_{1-8}$ alkyl)CO$_2$(C$_{1-8}$ alkyl), —NHSO$_2$(C$_{1-8}$ alkyl), —N(C$_{1-6}$ alkyl)SO$_2$(C$_{1-8}$ alkyl), —SO$_2$NHCO(C$_{1-8}$ alkyl), —CONHSO$_2$(C$_{1-8}$ alkyl), —CON(C$_{1-8}$ alkyl)(C$_{1-8}$ alkyl), —CO$_2$(C$_{1-8}$ alkyl), —S(C$_{1-8}$ alkyl), —SO(C$_{1-8}$ alkyl), —SO$_2$(C$_{1-8}$ alkyl), wherein C$_{1-8}$ alkyl, is defined as above,
  (iii) C$_{1-8}$ alkyl, wherein said C$_{1-8}$ alkyl is as defined above,
  (iv) —COR$_4$, wherein R$_4$ is as defined above,
  (v) —CONR$_4$R$_5$, wherein R$_4$ and R$_5$ are as defined above,
  (vi) —SO$_2$NR$_4$R$_5$, wherein R$_4$ and R$_5$ are as defined above or the groups R$_8$ and R$_9$, may be joined together to form a 4- to 8-membered monocyclic or bicyclic ring of which may contain:
    (a) one or two double bonds,
    (b) one or two oxo,
    (c) one or two O, S or N—R$_{10}$ wherein R$_{10}$ is hydrogen, C$_{1-8}$ alkyl, C$_{1-8}$ alkyl-Ar', wherein C$_{1-8}$ alkyl and Ar' are defined as above and Ar' is attached to any position of the $C_{1-8}$ alkyl group at any position or Ar', (d) one or two $R_1$.

2. A packaged pharmaceutical composition according to claim 1, where the compound has the formula:

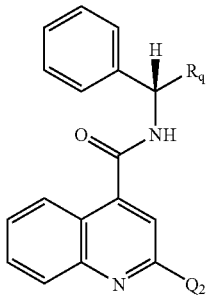

where $R_q$ is straight or branched chain alkyl having from 1–6 carbon atoms.

3. A packaged pharmaceutical composition according to claim 2 wherein:

$R_q$ is ethyl; and $R_8$ and $R_9$ are independently selected from:

hydrogen; $C_{1-8}$ alkyl, wherein said $C_{1-8}$ alkyl is as defined above; or $R_8$ and $R_9$ together form a 4- to 8-membered monocyclic or bicyclic ring which may contain:

(a) one or two double bonds;

(b) one or two oxo;

(c) one or two O, S or N—$R_{10}$ wherein $R_{10}$ is hydrogen, $C_{1-8}$ alkyl, $C_{1-8}$ alkyl-Ar', wherein $C_{1-8}$ alkyl and Ar' are defined as above and Ar' may be attached to $C_{1-8}$ alkyl at any position; or (d) one or two $R_1$ groups.

4. A packaged pharmaceutical composition according to claim 1, where the compound has the formula:

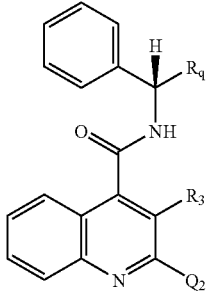

wherein:

$R_q$ is straight or branched chain alkyl having from 1–6 carbon atoms; and $R_3$ is $C_{1-6}$ alkyl or $C_{1-6}$ alkoxy.

5. A packaged pharmaceutical composition according to claim 4 wherein:

$R_q$ is ethyl; and $Q_2$ is a group of the formula:

wherein $R_8$ and $R_9$ together form a 4- to 8-membered monocyclic or bicyclic ring which may contain:

(a) one or two double bonds;

(b) one or two oxo;

(c) one or two O, S or N—$R_{10}$ wherein $R_{10}$ is hydrogen, or $C_{1-8}$ alkyl.

6. A packaged pharmaceutical composition according to claim 1, wherein the compound is:

(S)-N-(1-phenylpropyl)-2-(pyrrolidin-1-yl)-quinoline-4-carboxamide;

(S)-N-(1-phenylpropyl)-2-(piperidin-1-yl)-quinoline-4-carboxamide;

(S)-N-(1-phenylpropyl)-2-(1,2,5,6-tetrahydropyridin-1-yl)-quinoline-4-carboxamide;

(S)-N-(1-phenylpropyl)-2-(N,N-methylbenzylamino)-quinoline-4-carboxamide;

(S)-N-(1-phenylpropyl)-2-(homopiperidn-1-yl)-quinoline-4-carboxamide;

(S)-N-(1-phenylpropyl)-2-(1,2,3,4-tetrahydroisoquinolin-2-yl)-quinoline-4-carboxamide;

(S)-N-(1-phenylpropyl)-2-(morpholin-4-yl)-quinoline-4-carboxamide;

(S)-N-(1-phenylpropyl)-2-(thiomorpholin-4-yl)-quinoline-4-carboxamide;

(S)-N-(1-phenylpropyl)-2-(4-methylpiperidin-1-yl)-quinoline-4-carboxamide;

(S)-N-(1-phenylpropyl)-2-(3,3-dimethylpiperidin-1-yl)-quinoline-4-carboxamide;

(S)-N-(1-phenylpropyl)-2-(aza-1,4-dioxaspiro[4.5]decanyl-8-yl)-quinoline-4-carboxamide;

(S)-N-(1-phenylpropyl)-2-(N-methyl-N-n-butylamino)-quinoline-4-carboxamide;

(S)-N-(1-phenylpropyl)-2-(3,5,5-trimethylhomopiperidn-1-yl)-quinoline-4-carboxamide;

(S)-N-(1-phenylpropyl)-2-(2-methylpiperidn-1-yl)-quinoline-4-carboxamide;

(S)-N-(1-phenylpropyl)-2-(2-ethylpiperidn-1-yl)-quinoline-4-carboxamide;

(S)-N-(1-phenylpropyl)-2-(N-methyl-N-cyclohexylamino)-quinoline-4-carboxamide;

(S)-N-(1-phenylpropyl)-2-(N-n-propyl-N-cyclopropylmethylamino)-quinoline-4-carboxamide;

(S)-N-(1-phenylpropyl)-2-(N-ethyl-N-n-butylamino)-quinoline-4-carboxamide;

(S)-N-(1-phenylpropyl)-2-(4-methylpiperazin-1-yl)-quinoline-4-carboxamide;

(S)-N-(1-phenylpropyl)-2-(3-hydroxypyrrolidin-1-yl)-quinoline-4-carboxamide;

(S)-N-(1-phenylpropyl)-2-[(S)-2-methoxymethylpyrrolidin-1-yl]-quinoline-4-carboxamide;

(S)-N-(1-phenylpropyl)-2-[(S)-2-hydroxymethylpyrrolidin-1-yl]-quinoline-4-carboxamide;

(S)-N-(1-phenylpropyl)-2-(2-carboxypyrrolidin-1-yl)-quinoline-4-carboxamide;

(S)-N-(1-phenylpropyl)-2-(3-hydroxymethypiperidin-1-yl)-quinoline-4-carboxamide;

(S)-N-(1-phenylpropyl)-2-(2-hydroxymethypiperidin-1-yl)-quinoline-4-carboxamide;

(S)-N-(1-phenylpropyl)-2-(3-hydroxypiperidin-1-yl)-quinoline-4-carboxamide;

(S)-N-(1-phenylpropyl)-2-[2-(2-hydroxyethyl)piperidin-1-yl]-quinoline-4-carboxamide;
(S)-N-(1-phenylpropyl)-2-(N-α-methylbenzylamino)-quinoline-4-carboxamide;
(S)-N-(1-phenylpropyl)-2-(azabicyclo[3.2.2]nonan-3-yl)-quinoline-4-carboxamide;
(S)-N-(1-phenylpropyl)-3-methyl-2-(pyrrolidin-1-yl)-quinoline-4-carboxamide;
(S)-N-(1-phenylpropyl)-3-methyl-2-(piperidin-1-yl)-quinoline-4-carboxamide;
(S)-N-(1-phenylpropyl)-3-methoxy-2-(pyrrolidin-1-yl)-quinoline-4-carboxamide; or
(S)-N-(1-phenylpropyl)-3-methoxy-2-(piperidin-1-yl)-quinoline-4-carboxamide.

7. The packaged pharmaceutical composition of claim 1, wherein said patient is suffering from anxiety.

8. The packaged pharmaceutical composition of claim 1, wherein said patient is suffering from schizophrenia.

9. The packaged pharmaceutical composition of claim 1, wherein said patient is suffering from chronic pulmonary obstructive disorder.

10. The packaged pharmaceutical composition of claim 1, wherein said patient is suffering from pain.

11. The packaged pharmaceutical composition of claim 1, wherein said patient is suffering from depression.

* * * * *